United States Patent [19]

Moore

[11] Patent Number: 5,505,656
[45] Date of Patent: Apr. 9, 1996

[54] DENTAL INSTRUMENT SHARPENING GUIDE

[76] Inventor: Steven B. Moore, 7846 S. Logan St., Littleton, Colo. 80122

[21] Appl. No.: 182,732

[22] Filed: Jan. 14, 1994

[51] Int. Cl.$^6$ ............................................. B24B 33/00
[52] U.S. Cl. .................. 451/540; 451/552; 451/555; 76/82; 76/88
[58] Field of Search ................... 451/540, 552, 451/553, 555, 557, 558; 33/201; 76/82, 88; 433/25, 142, 229; 24/67.9, 531, 563; 403/213, 329, 397

[56] References Cited

U.S. PATENT DOCUMENTS

| | | | |
|---|---|---|---|
| 427,965 | 5/1890 | Brackett | 451/552 |
| 1,172,569 | 2/1916 | Sheafor | 451/557 |
| 1,425,446 | 8/1922 | Brown | 451/540 |
| 1,617,592 | 2/1927 | Hardy | 451/557 |
| 2,195,129 | 3/1940 | Hood | 451/555 |
| 2,462,637 | 2/1949 | Haydon | 451/558 |
| 3,721,049 | 3/1973 | Nakahara | 451/552 |
| 3,882,642 | 5/1975 | Sykes | 451/555 |
| 4,821,462 | 4/1989 | Moore | 451/555 |

*Primary Examiner*—Bruce M. Kisliuk
*Assistant Examiner*—Thomas W. Lynch
*Attorney, Agent, or Firm*—Richard W. Hanes

[57] ABSTRACT

Apparatus for manually sharpening dental instruments which require honing at a specific angle, comprising a planar base member having flat parallel sides and an elongated slot, a planar honing stone having flat parallel honing surfaces disposed within the slot of the base member perpendicularly to the plane of the base member and a spring clip positioned between one end of the slot and the honing stone for providing a biasing force to maintain the honing stone in pressure contact with the other end of the base member slot.

9 Claims, 2 Drawing Sheets

5,505,656

DENTAL INSTRUMENT SHARPENING GUIDE

The present invention relates to manual tool sharpening devices and more particularly to a hand held hone and guide combination for the sharpening of dental instruments.

BACKGROUND OF THE INVENTION

In an earlier U.S. Pat. No. 4,821,462, issued Apr. 18, 1989 for Dental Instrument Sharpening Hone, by the same inventor, a hone for reconditioning dental instruments is disclosed that is characterized by a planar abrasive surface supported upon a base alongside of which a protractor element is mounted for rotation. The protractor element displays one or more straight lines whose angular relation to the abrasive surface can be changed by rotation of the element with respect to the abrasive surface so that the line or lines can be set to have the same angle with respect to the abrasive surface as the handle of the instrument has to the cutting surface of the tool which is carried by the handle.

In operation, the protractor element is adjusted to the desired rotation and fixed therein so as to position and maintain the indicia lines at a desired angle to the hone, depending on what instrument is being sharpened. The cutting edge of the dental instrument is then laid upon the hone with the angle of the instrument's handle positioned parallel to the indicia reference lines on the protractor element. As the cutting edge is manually drawn across the abrasive surface the handle is maintained at its initial angle to the hone, that is parallel with the line or lines on the protractor element.

The foregoing device is well suited to its intended purpose, however the infinite adjustability of the reference lines with the circular protractor element does not lend itself to compactness and simplicity.

Therefore, the primary purpose of the present invention is to provide a tool sharpening guide with non-movable parts and a more simplistic and economical construction, albeit with several fixed angles of reference lines rather than the infinitely variable selection of the former invention.

Another object of the present invention is to provide an instrument sharpening tool that can withstand being sterilized in a customary autoclave at soak temperatures in the vicinity of 275 degrees fahrenheit.

A further object of the invention is to provide a manual sharpening hone containing a reference angle guide which doubles as a hand steadying rest throughout the sharpening stroke.

Other and further objects, features and advantages of the invention will become apparent upon a reading of the following detailed description of a preferred form of the invention, taken in connection with the accompanying drawings:

DESCRIPTION OF PREFERRED EMBODIMENT

Figure 1:
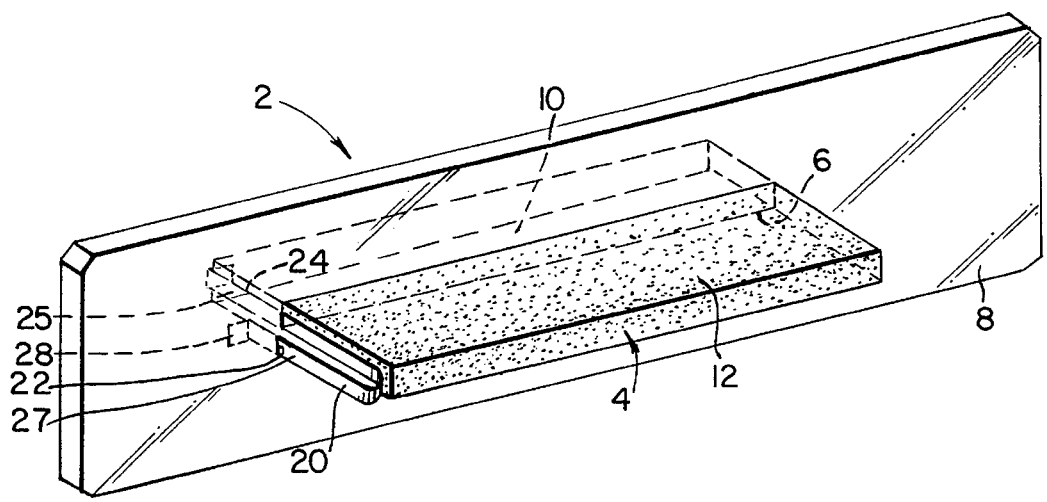
FIG. 1 is perspective view of the apparatus of the present invention. The vertically positioned reference guide base member is shown constructed of clear material so that it can been seen through and in FIG. 1 it is shown without the indicia lines or other printed material which is shown on the other figures.

The tool sharpening guide 2 comprises a rectangular, double faced abrasive sharpening stone 4 disposed in a slot 6 of the reference guide base 8 and perpendicular thereto. The sharpening stone may be constructed of a ceramic material such as aluminum magnesium silicate. Preferably, the reference guide base 8 bisects the top and bottom sharpening planes of the stone so as to provide four equally sized sharpening surfaces 10, 12, 14 and 16. Accordingly, upper and lower sharpening surfaces are then disposed on each side of the reference guide base.

A stainless steel spring clip 20 interacting between one end 22 of the slot 6 and the end surface 24 of the stone 4 maintains the abrasive sharpening stone in its position in the slot. The spring 20 is a substantially "U" shaped leaf spring with one stem, or upright stroke, 25 of the "U" being approximately twice the length of the shorter stem 27. The longer stem 25 lays flat against one end edge surface 24 of the stone 4, terminating in a bent over end 26 which wraps around the corner of the stone and lays against its lateral longitudinal edge 30. The main body portion of the spring clip 20 lies on one side of the reference guide base with the short stem 27 of the spring projecting through the slot 6 and having the end 28 of the short stem bent at a right angle so as to wrap around the end of the slot and lay against the face of the reference guide base which is opposite to the side of the base on which the main body portion of the spring is disposed. The clip spring arrangement as described retains the stone within the slot through the bias of the spring, forcing the stone against the end of the slot opposite to the end which is in contact with the spring. The bent ends 26 and 28 of the spring 20 prevent lateral movement of the stone 4 in one direction but permit it under firm pressure in the opposite direction for removal of the stone from the reference guide base.

Figure 2:
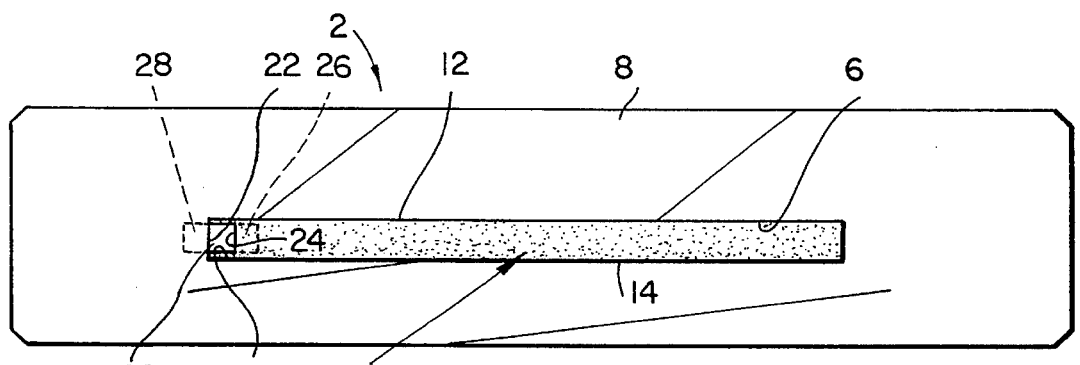
FIG. 2 is a side elevational view of the device of the present invention.
Figure 3:
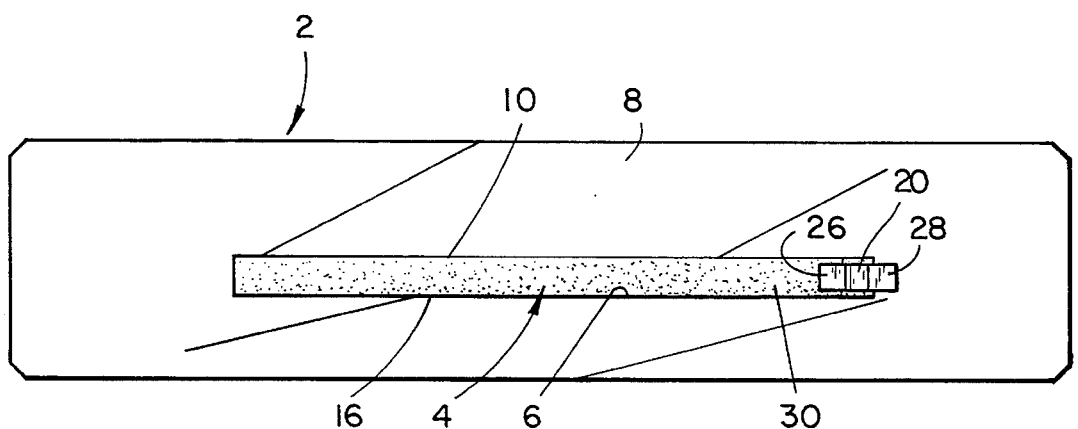
FIG. 3 is a side elevational view of the side opposite to that shown in FIG. 2.
Figure 4:
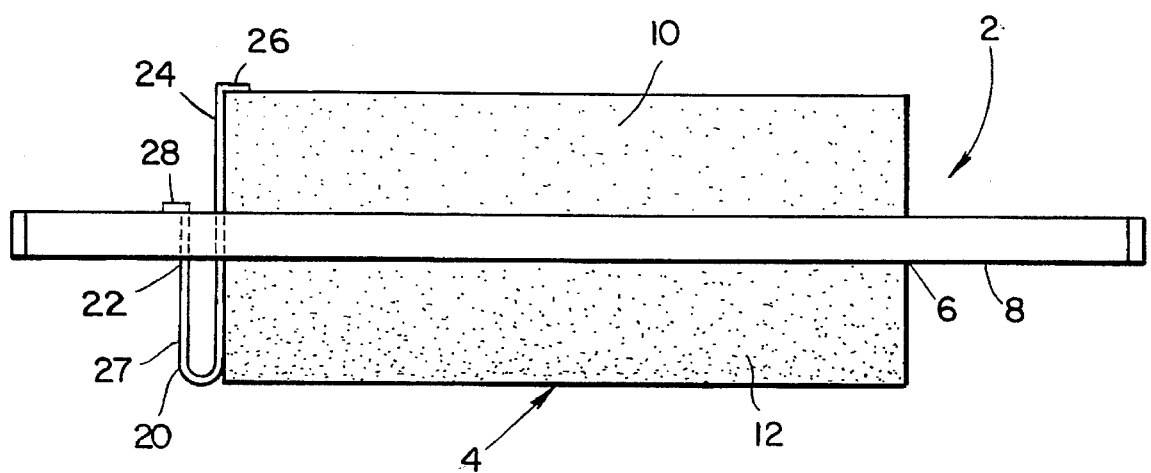
FIG. 4 Is a top view of the device of the present Invention

The faces of the reference guide base are etched or otherwise marked with indicia guide lines 35, each having an angle to the sharpening surfaces of the hone 4 which is identical to the angle of a particular dental instrument's handle to the planar surface of its cutting tool. To sharpen a dental tool, the correct angle of the handle to the sharpening surface is first determined by reference to the information which may be printed on the guide base, as shown in FIGS. 2 and 3, or obtained elsewhere. When the proper angle is known the tool is laid upon the abrasive surface of the sharpening stone with the handle of the instrument positioned in alignment with or parallel to the appropriately angled one of the guide lines 35. If the handle of the instrument is kept parallel to the proper reference line as the cutting surface of the tool is drawn across the hone, the tool will be reconditioned with the proper angle.

It should be appreciated that the slot 6 in the guide base is not located exactly midway between the upper and lower edges of the base. For the lower handle angles of, for example, 10 and 20 degrees it is more appropriate to position the flat upper edge of the guide base closer to the surface of the hone. This positioning provides a proper hand rest, or railing, for supporting the hand while holding the instrument handle at these lower angles as the instrument is drawn across the sharpening surface. However, on the opposite side of the stone 4 the edge of the guide base is somewhat more elevated from the abrasive surface, thus providing a similar railing for the continuous support and steadying of the hand as the higher angle instruments are sharpened. Additional timing of the support for the instrument can come from maintaining the instrument in contact with the side face of the guide base as it is moved across the stone.

Because the reference guide base 8 is substantially reduced in size from the large rotatable protractor reference guide of the prior invention, it is economically feasible to use the more expensive high temperature plastic that can withstand the high temperatures of sterilizing autoclaves. One such material is a plastic made of polysulfone, by "Amoco" having a tolerance for continuous temperatures of at least 300 degrees fahrenheit. By the use of such materials the sharpening device can be placed with other instruments into an autoclave for sterilization without fear of damage to the apparatus.

I claim:

1. Apparatus for manually sharpening dental instruments, comprising:
   - a planar base member having flat parallel sides and an elongated slot therethrough having first and second ends;
   - a planar honing stone having flat parallel honing surfaces and disposed within the said slot perpendicularly to the plane of the base member so as to project from each of the sides of the base member; and
   - a spring clip positioned between the first end of the said slot and the honing stone for providing a biasing force to maintain the honing stone in pressure contact with the second end of the said slot.

2. The combination of claim 1 wherein the base member is provided with at least one indicia forming reference line positioned angularly to the honing surfaces of the stone.

3. The combination of claim 2 where the spring clip is generally "U" shaped with first and second stems and where the ends of the stems are bent perpendicularly to the stems.

4. The combination of claim 3 where the bent perpendicular end of the first stem lays against the surface of one side of the base member and the bent perpendicular end of the second stem lays against the stone in a position parallel to the said slot.

5. The combination of claim 1 wherein the base material is heat tolerant to a temperature of 300 degrees fahrenheit.

6. The combination of claim 5 wherein the base material is transparent.

7. The combination of claim 6 wherein the base member is provided with a plurality of indicia forming reference lines, each positioned angularly to the honing surfaces of the stone and where the spring clip is generally "U" shaped with first and second stems each of whose ends are bent perpendicularly to the stems and where the bent perpendicular end of the first stem lays against the surface of one side of the base member and the bent perpendicular end of the second stem lays against the stone in a position parallel to the said slot.

8. The combination of claim 7 where the base member includes first and second parallel sides which are mutually parallel to the slot for providing hand supporting rails.

9. The combination of claim 8 where the distance between the honing stone and the first parallel side of the base is unequal to the distance between the honing stone and the second parallel side of the base.

* * * * *